United States Patent [19]

Sheaff et al.

[11] 4,055,470

[45] Oct. 25, 1976

[54] DEVICE FOR EXAMINING BIOLOGICAL SPECIMENS

[75] Inventors: Edward Thomas Sheaff; Norman Alexander Hinton, both of Toronto, Canada

[73] Assignee: K-Vet Limited, Cambridge, Canada

[21] Appl. No.: 694,077

[22] Filed: June 9, 1976

[30] Foreign Application Priority Data

June 10, 1975 Canada .................................. 229154

[51] Int. Cl.² .............................................. C12K 1/00
[52] U.S. Cl. .................................... 195/127; 356/244
[58] Field of Search .................... 195/127; 350/238; 356/244

[56] References Cited

U.S. PATENT DOCUMENTS

| | | | |
|---|---|---|---|
| 1,829,472 | 10/1931 | Buck, Jr. .............................. | 195/127 |
| 3,493,772 | 2/1970 | Daughters et al. .................. | 356/244 |
| 3,962,040 | 6/1976 | Campbell et al. .................... | 195/127 |

*Primary Examiner*—Alvin E. Tanenholtz
*Attorney, Agent, or Firm*—Fetherstonhaugh & Co.

[57] ABSTRACT

A device for reading and recording the sensitivity of a series of specimens wherein a test plate is inoculated with a series of specimen organisms at predetermined spaced sites thereon, incubated, and the clone at each site examined to determine whether the organism is sensitive or resistant to the test antibiotic or positive or negative with respect to a test biochemical having a frame, a mount for a plurality of test plates arranged in a predetermined pattern, mounting means for mounting said mount in said frame for movement along an X axis and Y axis, control means for moving said mount in said mounting means along the X axis and the Y axis, a viewing plate on said frame above said mount, a viewing system for each plate on said mount terminating in a viewing opening at said viewing plate for viewing the specimens one at a time on its respective plate in said mount, said control means being adapted to move said mount in said mounting means as aforesaid with preset sequential incremental movements to move each of the series of specimens and each plate into the field of its respective viewing system in turn for viewing through said lens system which incorporates the improvement of a positive signal terminal on said plate adjacent each viewing opening of said viewing means, a negative signal terminal on said plate adjacent each viewing opening of said viewing means, manually operable means for actuating said positive and said negative signal terminals, means for transmitting signals from said positive signal terminal and from said negative signal terminal to signal recording means, and means on said viewing plate for indicating when a signal from said positive or said negative signal terminal has been transmitted to said recording means by said means for transmitting signals.

4 Claims, 5 Drawing Figures

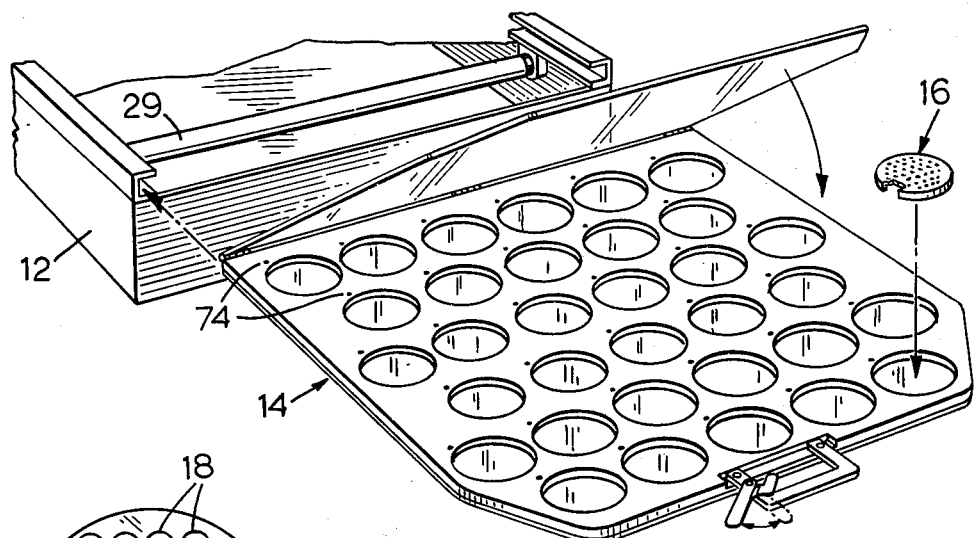
FIG. 2
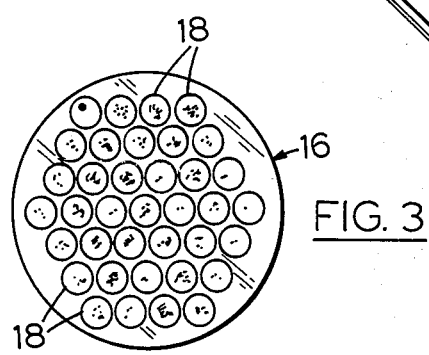
FIG. 3
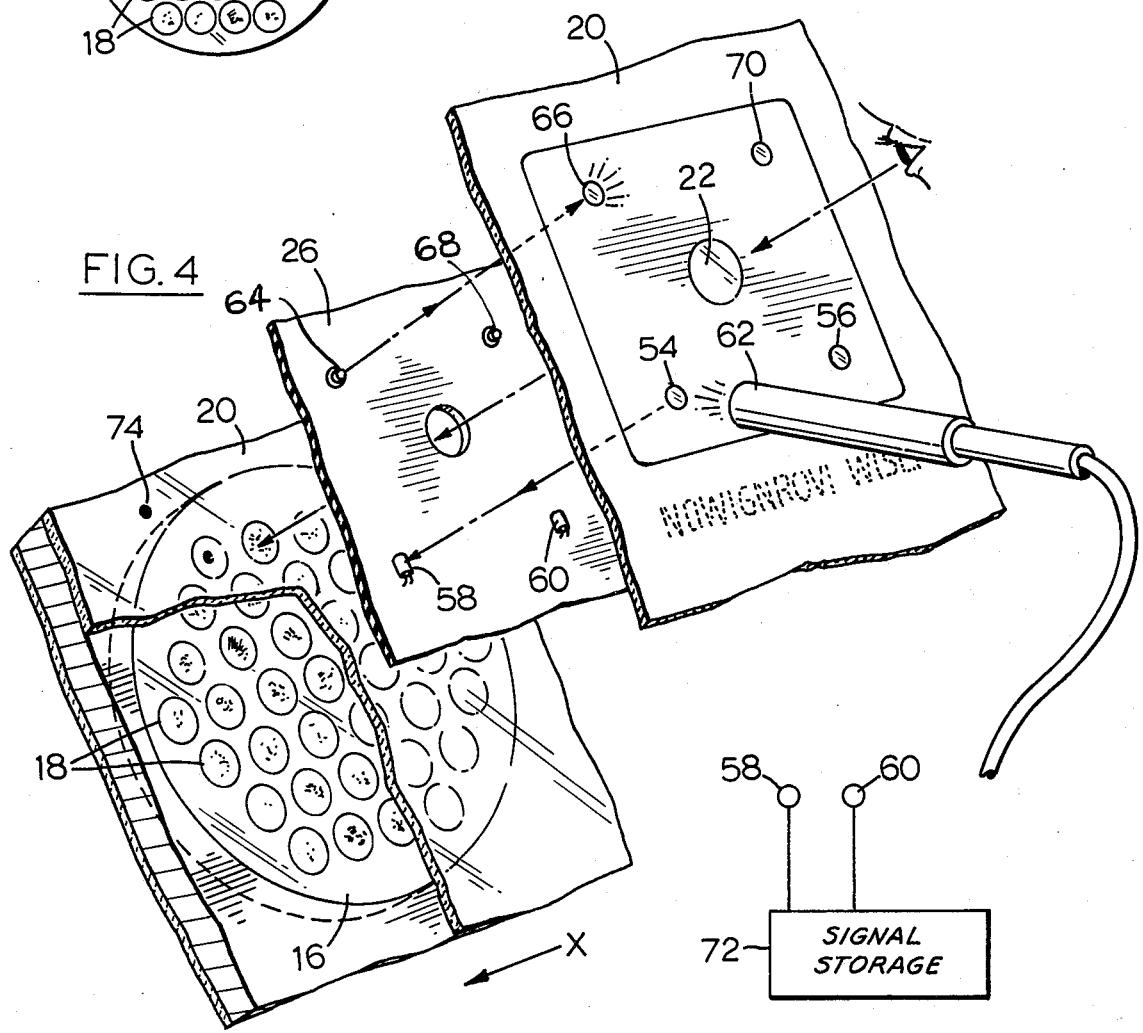
FIG. 4
FIG. 5

DEVICE FOR EXAMINING BIOLOGICAL SPECIMENS

This invention relates to a device for recording the antibiotic sensitivity and identity of a series of bacterial specimens on solid media contained on petri plates.

The ever increasing demands placed on clinical bacteriology laboratory coupled with budgetary limitations necessitate a search for inexpensive means of mechanizing certain aspects of bacteriology work load. This invention is a mechanical device designed to achieve a rapid and accurate examination and recordal of antibiotic sensitivity and biochemcial test results. It permits the operator to quickly examine a series of specimens in a systematic manner and to record his observations with assurance that they have been recorded.

This invention relates to a device for reading and recording the antibiotic sensitivity and biochemical test results of a series of specimens wherein a test antibiotic or biochemical medium is inoculated with a series of specimen organisms at predetermined spaced sites thereon, incubated, and the clone at each site examined to determine whether the arganism is sensitive or resistant to the test antibiotic or positive or negative with the test biochemical that has a frame, a mount for a plurality of test plates arranged in a predetermined pattern, mounting means for mounting said mount in said frame for movement along an X axis and a Y axis, control means for moving said mount in said mounting means along the X axis and the Y axis, a viewing plate on said frame above said mount, a viewing system for each plate on said mount terminating in a viewing opening at said viewing plate for viewing the specimens one at a time on its respective plate in said mount, said control means being adapted to move said mount in said mounting means as aforesaid with preset sequential incremental movements to move each of the series of specimens on each plate into the field of its respective viewing system in turn for viewing through said lens system and comprises the improvement of a positive signal terminal on said plate adjacent each viewing opening of said viewing means, a negative signal terminal on said plate adjacent each viewing opening of said viewing means, manually operable means for actuating said positive and said negative signal terminals, signals from said positive signal terminal and said negative signal terminal being transmittable to a signal recording means adapted to record signals in respect of the plates to which said signals are adjacent and means on said viewing plate for indicating when a signal from said positive or said negative signal terminal has been recorded by said recording means. The invention will be clearly understood after reference to the following specification read in conjunction with the drawings.

In the drawings:

FIG. 2 is a partial perspective view illustrating the manner in which test plates are mounted in a tray and then mounted in the device of the invention;

FIG. 3 is an illustration of a test plate;

FIG. 4 is an exploded view illustrating the viewing system of the embodiment illustrated in the drawings; and FIG. 5 is a schematic illustration of the electronic storage of information transmitted from the device of the invention.

Figure 1:
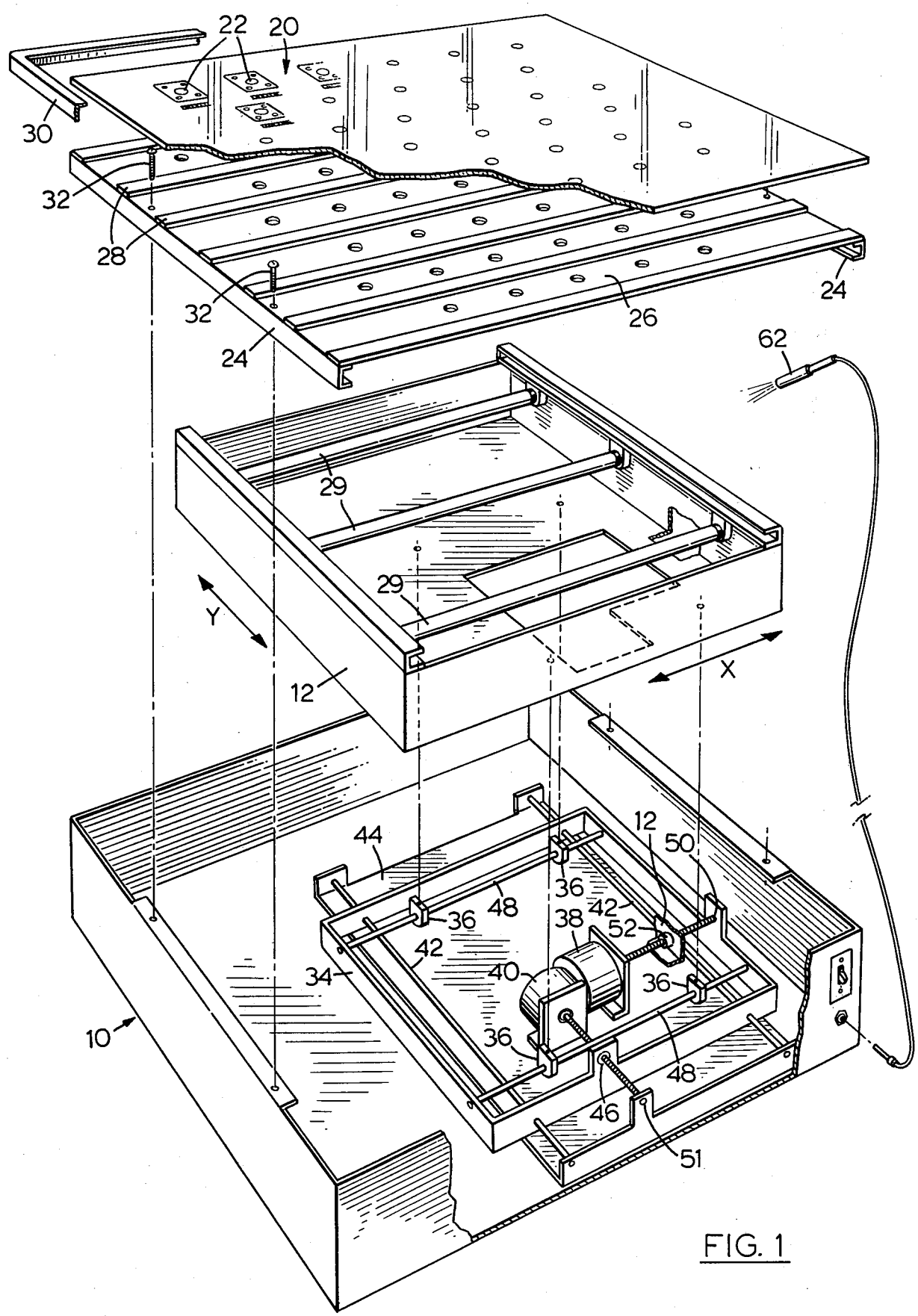
FIG. 1 is an exploded view of principal parts of a device according to the invention.

Referring to the drawings, the device there illustrated comprises a frame 10 and a mount 12 for a tray 14 that has a plurality of openings each designed to receive a test plate 16 that has a series of sites 18 at predetermined spaced apart locations that, in use, contain bacterial specimens which have been incubated. It is desired to determine the clone at each location to determine whether or not the particular specimen is sensitive or resistant to a test antibiotic or positive or negative for the test biochemical which is also contained on the plate. The general method of testing is well known and this invention does not claim the general method to be new. The invention is concerned with the device for examining the clone at each of the site locations 18 in each of the plates 16 in each of the openings in the tray 14.

The specimens in each of the sites 18 are examined through a viewing system and there is a viewing system for each of the plates 16. Each viewing system terminates at a viewing opening 22 on the viewing plate 20 and openings 22 each align with an opening in sheet 26 to provide a direct line of sight to the clones at the sites 18 on the plates 16.

The viewing plate 20 is made of an opaque glass that is provided with clear areas at viewing openings 22 that form the termination of the viewing systems for the plates 16 and clear areas 66 and 70 through which light signals are transmitted in use as will be referred to later. It is carried by a frame that is formed from side members 24 secured together by a sheet of dielectric material 26. Strips of dielectric material 28 space the viewing plate 20 from the dielectric sheet 26 and provide a series of parallel spaces between plates 20 and 26 within which electronic components associated with the use of the device can be mounted. Tubular lights 29 provide illumination.

A frame moulding 30 extends around the components of the top structure just described to contain the glass sheet 20 on the strips 28 after the dielectric sheet has been secured to the base by means of the screw 32.

Mount 12, which is designed to receive the tray 14 of plates 16 in use, is bolted to a central assembly that is carried by the frame 10 and that provides for controlled movement thereof in an X and a Y direction. The mount is secured to the support blocks 36 by means of bolts that pass through holes in its bottom surface and which align with the blocks, as indicated in FIG. 1.

Control assembly comprises sub-frame 44 which is secured to frame 10 and sub-frame 34. Sub-frame 34 is slidably mounted on rods 42 for sliding movement in the Y axis direction with respect to sub-frame 44 and main frame 10. Support blocks 36 which carry frame 12 are slidable on rods 48 in the direction of the X axis. Thus, frame 12 can move in the direction of the X axis and in the direction of the Y axis on rods 48 and 42 respectively.

Stepping motors 38 and 40 control the movement of the mount 12 with respect to the frame 10 in the directions of the X and the Y directions respectively. The motors 38 and 40 are each rigidly mounted on frame 10 and each have threaded shafts, the free ends of which are journalled in sub-frame 34 as at 50 and in sub-frame 44 as at 51, respectively. The threaded portions of their shafts threadedly engage with nuts 52 and 46, respectively, that are journalled in the mount 12 and sub-frame 34, respectively. It will be apparent that rotation of the shaft of motor 38 will result in motion of the mount 12 in an X direction and rotation of the shaft of motor 40 will result in motion of the mount 12 in a Y direction.

Thus, by operation of the motors 38 and 40 one can move the mount 12 in either an X or a Y direction.

Motors 38 and 40 are programmed electronically to move the mount 12 along their respective X and Y axes and carry each of the specimen sites 18 of the plates 16 under the viewing opening 22 of its respective viewing system.

There is a viewing system that terminates in a viewing opening 22 on the viewing plate 20 for each of the plates 16 that is mounted in the tray 16 of the mount 12. When the motors 38 and 40 are moved to the beginning position the specimen at the upper left hand site 18 of each plate 16 is lined up for viewing through a viewing opening 22. When this site at each viewing opening has been examined the X motor moves the mount 12 to expose to view the site 18 to the right of the one first looked at. When this site has been examined the motor again operates to move to the next following site. It will be apparent that movement in the X direction only is sufficient to view the first four sites. However, the fifth site requires movement in the Y as well as the X direction. The motors are programmed to move the mount incrementally to view in sequence each of the sites 18 of the antibiotic plate 16.

Motors 38 and 40 are stepping motors and, in use, their shafts rotate a pre-determined amount each time they are pulsed with electric power. The motors in the embodiment illustrated have shafts which turn 1.8° each time they are pulsed.

Thus, in order to achieve one complete revolution of the shaft of the stepping motors 38 and 40, one must arrange to pulse the motor 200 times. One relolution of the motor achieves an X or a Y movement of one-eighth of an inch in the embodiment of the invention illustrated.

The sites 18 on the test plates 16 are spaced apart a distance in the X direction that requires 750 steps of the X direction pulse motor to move the frame to locate successive sites in any horizontal row in the field of view of the viewing system 22 for the plates.

The rows are spaced apart in a Y direction a distance that requires 645 pulses of the Y motor 40. It will also be noted that the rows are displaced in an X direction so that when one moves from the last site in an X row and proceeds to the next following site in the underlying Y row, one must arrange for amovement in the X direction as well as the Y direction. In this connection, the spacing apart of the sites in the X direction is one half of the spacing apart of the individual sites in a row. Thus, when one wants to move from the last site in an X direction down to the next site in the underlying row, one must arrange to move the plate within 375 pulses of the X direction motor and 645 pulses of the Y direction motor.

The stepping motors are programmed to move the sites in predetermined succession under their respective viewing systems upon actuation of a manually accessible control. Thus the operator can control the rate at which the sites of each plate are moved under the viewing system for the plate in accordance with a predetermined pattern. The electronic system for programming the movement of the trays in the X and Y direction to bring the individual sites under the viewing system in a predetermined order is a matter of design within the knowledge of any skilled electronics engineer. It is not illustrated in this application and does not, of itself, form part of the invention.

The signals transmitted to the signal devices 58 and 60 are transmitted to a computer signal storage 72 where they are stored. The computer storage device can be designed to do many things with the information it receives including the interpretation of the results. This invention is not concerned with the storage or interpretation of the results but only with the mechanical means for effeciently transferring the results to the computer.

It is desired to record either a positive or a negative indication for each of the sites of each of the plates and this is achieved by a positive signal terminal 54 and a negative signal terminal 56 adjacent each viewing opening 22. The signal terminals 54 and 56 are openings through the opaque glass designed to admit light from a light source 62 therethrough which activates light sensitive cells 58 and 60 respectively. If, for example, the operator on viewing the clone in the underlying site through opening 22 sees a positive indication, he directs the beam from a probe light 62 through opening 54 to activate cell 58. Activation of cell 58 causes signal lamp 64 to be illuminated and it is visible through opening 66 to tell the operator that he has been successful in recording a positive indication. A negative indication is similarly recorded by directing the beam from light 62 through the opening 56 to activate negative signal light sensitive device 60. Operation of the device 60 illuminates signal light 68 which is visible through opening 70 to tell the operator that he has been successful in recording a negative signal.

In use, the invention is used to record the results of the sensitivity of unknown bacterial specimens to predetermined antibiotics or biochemical mediums. Plates 16 are each innoculated with some 37 different cultures at predetermined spaced sites 18 which become the clones when they grow. Each plate contains a predetermined concentration of antibiotic or formulation of biochemical. Each of the openings in the tray 14 is adapted to receive a plate 16 and each of the plates has a different antibiotic or biochemical test medium.

The bacterial cultures to be tested are incubated in accordance with standard practice and each site 18 of each plate 16 is loaded with a different bacterial culture. Thus, a small amount of each of some 36 cultures can be deposited at the sites of the plates. Site No. 1 is a locating site and merely carries an india ink marking as indicated by the dot in the upper lefthand corner and it is used to orient the plates with respect to the tray 14. One merely aligns the india ink dot on the first site with the india ink dot 74 on the tray so that the sites are all in a predetermined position with respect to the tray and with respect to the mount 12 when the tray is slid into the mount. After the plates have been mounted in the tray, the cover is closed thereon and the tray is slid into the mount 12 as indicated in FIG. 2. The motors 38 and 40 are then operated to locate the first site which is marked with an india ink dot under the viewing opening 22 of its respective plate. The operator then looks through each of the viewing openings on the viewing plate 20 to check for the site with a dot and on seeing it directs the light probe through the positive signal opening 54 to actuate the signal device 58 and record on the signal storage device the information that that particular plate is properly orient. The operator looks for the indication of an illumination in opening 66 to indicate to him that the signal device has been operated and a signal appropriately received by the signal storage. Light 64 is a light source that is activated upon the transmission of a signal to the signal storage.

The operator then operates a lever which activates the motor 38 to move the mount 12 and all of the plates 16 carried in the tray thereof one space in the X direction to locate the No. 2 site of all plates under their respective viewing openings. The operator again views the site under each viewing opening 22 in the plate 20 to see whether there is a positive or a negative biological reaction at the underlying site and records either a positive or a negative reaction by shining the light through either the positive or negative signal openings 54 and 56. After each recording, the operator checks the signal lights 64 and 68 and then moves the mount one step further by manual operation of the lever.

The embodiments of the invention in which an exclusive property or privilege is claimed are defined as follows:

1. In a device for reading and recording the sensitivity of a series of specimens wherein a test plate is inoculated with a series of specimen organisms at predetermined spaced sites thereon, incubated, and the clone at each site examined to determine whether the organism is sensitive or resistant to the test antibiotic or positive or negative with respect to a test biochemical having a frame, a mount for a plurality of test plates arranged in a predetermined pattern, mounting means for mounting said mount in said frame for movement along an X axis and Y axis, control means for moving said mount in said mounting means along the X axis and the Y axis, a viewing plate on said frame above said mount, a viewing system for each plate on said mount terminating in a viewing opening at said viewing plate for viewing the specimens one at a time on its respective plate in said mount, said control means being adapted to move said mount in said mounting means as aforesaid with preset sequential incremental movements to move each of the series of specimens and each plate into the field of its respective viewing system in turn for viewing through said lens system the improvement which comprises a positive signal terminal on said plate adjacent each viewing opening of said viewing means, a negative signal terminal on said plate adjacent each viewing opening of said viewing means, manually operable means for actuating said positive and said negative signal terminals, means for transmitting signals from said positive signal terminal and from said negative signal terminal to signal recording means, and means on said viewing plate for indicating when a signal from said positive or said negative signal terminals has been transmitted to said recording means by said means for transmitting signals.

2. In a device for reading and recording the sensitivity of a series of specimens as claimed in claim 1 in which said positive signal terminal and said negative signal terminal each comprise a light responsive device under said plate and a light path from said device and terminating on said plate adjacent each viewing opening as aforesaid, said manually operable means for operating said positive and negative signals comprising a light source for transmitting light through said light path to said light sensitive device.

3. In a device for reading and recording the sensitivity of a series of specimens as claimed in claim 1 having means sensitive by an operator for indicating when said negative signal terminals and said positive signal terminals have been operated.

4. In a device for reading and recording the sensitivity of a series of specimens as claimed in claim 2 having means sensitive by an operator for indicating when said negative signal terminals and said positive signal terminals have been operated.

* * * * *